US008945010B2

(12) United States Patent
Semler

(10) Patent No.: US 8,945,010 B2
(45) Date of Patent: Feb. 3, 2015

(54) METHOD OF EVALUATING CONSTIPATION USING AN INGESTIBLE CAPSULE

(75) Inventor: John R Semler, Williamsville, NY (US)

(73) Assignee: Covidien LP, Mansfield, MA (US)

( * ) Notice: Subject to any disclaimer, the term of this patent is extended or adjusted under 35 U.S.C. 154(b) by 366 days.

(21) Appl. No.: 12/971,989

(22) Filed: Dec. 17, 2010

(65) Prior Publication Data

US 2011/0257490 A1    Oct. 20, 2011

Related U.S. Application Data

(60) Provisional application No. 61/289,867, filed on Dec. 23, 2009.

(51) Int. Cl.
*G06F 19/00* (2011.01)
*A61B 5/00* (2006.01)
(Continued)

(52) U.S. Cl.
CPC ........... *A61B 5/14539* (2013.01); *A61B 5/0002* (2013.01); *G06F 19/34* (2013.01); *A61B 5/036* (2013.01); *A61B 5/073* (2013.01); *A61B 5/42* (2013.01); *A61B 5/6861* (2013.01)
USPC ............ 600/301; 600/300; 600/302; 128/898

(58) Field of Classification Search
None
See application file for complete search history.

(56) References Cited

U.S. PATENT DOCUMENTS 3,683,389 A    8/1972 Hollis
3,719,183 A    3/1973 Schwartz
(Continued)

FOREIGN PATENT DOCUMENTS

DE    34 40 177.6    5/1986
DE    10018341       8/2001
(Continued)

OTHER PUBLICATIONS

Rao, Satish S.C., et. al., Investigation of Colonic and Whole-Gut Transit With Wireless Motility Capsule and Radiopaque Markers in Constipation, Clinical Gastroenterology and Hepatology, vol. 7, Iss 5, May 2009, p. 537-544, ISSN 1542-3565, http://dx.doi.org/10.1016/j.cgh.2009.01.017. http://www.sciencedirect.com/science/article/pii/S1542356509000615.*

(Continued)

*Primary Examiner* — William Thomson
*Assistant Examiner* — Davin Sands
(74) *Attorney, Agent, or Firm* — Pearl Cohen Zedek Latzer Baratz LLP

(57) ABSTRACT

A method for diagnosing constipation comprising the steps of providing an ingestible capsule (20) having a given density and a pH sensor (22) and a temperature sensor (24), having a subject ingest the capsule, recording pH measurements from the pH sensor as a function of time as the capsule moves through at least a portion of the gastrointestinal tract of the subject, transmitting the pH measurements to a processor (19) outside of the gastrointestinal tract of the subject, recording temperature measurements from the temperature sensor as a function of time as the capsule moves through at least a portion of the gastrointestinal tract of the subject, transmitting the temperature measurements to a processor (19) outside of the gastrointestinal tract of the subject, determining transit time of the capsule between a first location in the gastrointestinal tract of the subject and a second location in the gastrointestinal tract of the subject as a function of the pH measurements and the temperature measurements, providing a reference transit time that is a function of the density of the capsule, and comparing the determined transit time to the reference transit time to evaluate the subject for constipation.

16 Claims, 11 Drawing Sheets

Example of the capsule system and ROMs recording in a healthy subject. The healthy subject shows normal GET at 2.5 hours, normal SBTT at 5.3 hours, and normal CTT at 15.5 hours, and 4 ROMs on the day 2 radiograph.

(51) Int. Cl.
*A61B 5/145* (2006.01)
*A61B 5/03* (2006.01)
*A61B 5/07* (2006.01)

(56) References Cited

U.S. PATENT DOCUMENTS

| | | | |
|---|---|---|---|
| 3,723,644 A | 3/1973 | Haskell et al. |
| 3,971,362 A | 7/1976 | Pope et al. |
| 4,177,800 A | 12/1979 | Enger |
| 4,239,040 A | 12/1980 | Hosoya |
| 4,246,784 A | 1/1981 | Bowen |
| 4,278,077 A | 7/1981 | Mizumoto |
| 4,431,005 A | 2/1984 | McCormick |
| 4,439,197 A | 3/1984 | Honda et al. |
| 4,631,582 A | 12/1986 | Nagasaki et al. |
| 4,681,093 A | 7/1987 | Ono et al. |
| 4,689,621 A | 8/1987 | Kleinberg |
| 4,741,327 A | 5/1988 | Yabe |
| 4,784,155 A | 11/1988 | Mills |
| 4,844,076 A | 7/1989 | Lesho et al. |
| 4,854,328 A | 8/1989 | Pollack |
| 4,915,113 A | 4/1990 | Holman |
| 4,936,823 A | 6/1990 | Colvin et al. |
| 5,004,614 A | 4/1991 | Staniforth |
| 5,088,492 A | 2/1992 | Takayama et al. |
| 5,233,997 A | 8/1993 | Klein et al. |
| 5,279,607 A | 1/1994 | Schentag et al. |
| 5,318,557 A | 6/1994 | Gross |
| 5,324,280 A | 6/1994 | Wong et al. |
| 5,330,427 A | 7/1994 | Weissenburger |
| 5,395,366 A | 3/1995 | D'Andrea et al. |
| 5,558,640 A | 9/1996 | Pfeiler et al. |
| 5,572,252 A | 11/1996 | Naka et al. |
| 5,585,840 A | 12/1996 | Watanabe et al. |
| 5,596,366 A | 1/1997 | Takashima et al. |
| 5,604,531 A | 2/1997 | Iddan et al. |
| 5,697,384 A | 12/1997 | Miyawaki et al. |
| 5,738,110 A | 4/1998 | Beal et al. |
| 5,749,830 A | 5/1998 | Kaneko et al. |
| 5,782,747 A | 7/1998 | Zimmon |
| 5,819,736 A | 10/1998 | Avny et al. |
| 5,833,603 A | 11/1998 | Kovacs et al. |
| 5,853,005 A | 12/1998 | Scanlon |
| 5,873,830 A | 2/1999 | Hossack et al. |
| 5,906,579 A | 5/1999 | Vander Salm et al. |
| 5,972,389 A | 10/1999 | Shell et al. |
| 5,976,571 A | 11/1999 | Crison et al. |
| 5,993,378 A | 11/1999 | Lemelson |
| 6,053,873 A | 4/2000 | Govari et al. |
| 6,074,349 A | 6/2000 | Crowley |
| 6,165,128 A | 12/2000 | Cespedes et al. |
| 6,172,640 B1 | 1/2001 | Durst et al. |
| 6,183,466 B1 | 2/2001 | Wong et al. |
| 6,185,443 B1 | 2/2001 | Crowley |
| 6,188,355 B1 | 2/2001 | Gilboa |
| 6,219,091 B1 | 4/2001 | Yamanaka et al. |
| 6,240,312 B1 | 5/2001 | Alfano et al. |
| 6,254,531 B1 | 7/2001 | Higuchi et al. |
| 6,346,269 B1 | 2/2002 | Hsiao et al. |
| 6,364,829 B1 | 4/2002 | Fulghum |
| 6,402,689 B1 | 6/2002 | Scarantino et al. |
| 6,428,469 B1 | 8/2002 | Iddan et al. |
| 6,462,770 B1 | 10/2002 | Cline et al. |
| 6,584,348 B2 | 6/2003 | Glukhovsky |
| 6,599,284 B2 | 7/2003 | Faour |
| 6,607,301 B1 | 8/2003 | Glukhovsky et al. |
| 6,635,834 B1 | 10/2003 | Wenner |
| 6,667,765 B1 | 12/2003 | Tanaka |
| 6,709,387 B1 | 3/2004 | Glukhovsky et al. |
| 6,900,790 B1 | 5/2005 | Doi et al. |
| 6,934,573 B1 | 8/2005 | Glukhovsky et al. |
| 6,939,292 B2 | 9/2005 | Mizuno |
| 6,947,788 B2 | 9/2005 | Gilboa et al. |
| 7,022,067 B2 | 4/2006 | Glukhovsky et al. |
| 7,083,578 B2 | 8/2006 | Lewkowicz et al. |
| 7,112,752 B1 | 9/2006 | Wenner |
| 7,118,529 B2 | 10/2006 | Glukhovsky et al. |
| 7,160,258 B2 | 1/2007 | Imran et al. |
| 7,195,778 B2 | 3/2007 | Fleshner-Barak et al. |
| 7,214,182 B2 | 5/2007 | Shimizu et al. |
| 7,228,166 B1 | 6/2007 | Kawasaki et al. |
| 7,251,383 B2 | 7/2007 | Iddan |
| 7,295,226 B1 | 11/2007 | Meron et al. |
| 7,316,647 B2 | 1/2008 | Kimoto et al. |
| 7,355,625 B1 | 4/2008 | Mochida et al. |
| 7,419,468 B2 | 9/2008 | Shimizu et al. |
| 7,511,733 B2 | 3/2009 | Takizawa |
| 7,724,928 B2 | 5/2010 | Glukhovsky et al. |
| 7,970,455 B2 | 6/2011 | Zilberstein et al. |
| 8,216,130 B2 | 7/2012 | Glukhovsky et al. |
| 2001/0017649 A1 | 8/2001 | Yaron |
| 2001/0035902 A1 | 11/2001 | Iddan et al. |
| 2001/0038831 A1 | 11/2001 | Park et al. |
| 2001/0045899 A1 | 11/2001 | Hoek |
| 2001/0051766 A1 | 12/2001 | Gazdzinski |
| 2002/0042562 A1 | 4/2002 | Meron et al. |
| 2002/0099310 A1 | 7/2002 | Kimchy et al. |
| 2002/0103417 A1 | 8/2002 | Gazdzinski |
| 2002/0103425 A1 | 8/2002 | Mault |
| 2002/0132226 A1 | 9/2002 | Nair et al. |
| 2002/0144154 A1 | 10/2002 | Tomkow |
| 2002/0160043 A1 | 10/2002 | Coleman |
| 2002/0198439 A1 | 12/2002 | Mizuno |
| 2002/0198470 A1 | 12/2002 | Imran et al. |
| 2003/0040685 A1 | 2/2003 | Lewkowicz et al. |
| 2003/0043263 A1 | 3/2003 | Glukhovsky et al. |
| 2003/0077223 A1 | 4/2003 | Glukhovsky et al. |
| 2003/0114742 A1 | 6/2003 | Lewkowicz et al. |
| 2003/0117491 A1 | 6/2003 | Avni et al. |
| 2003/0144570 A1 | 7/2003 | Hunter et al. |
| 2003/0167000 A1 | 9/2003 | Mullick et al. |
| 2003/0191430 A1* | 10/2003 | D'Andrea et al. ............... 604/66 |
| 2003/0195415 A1 | 10/2003 | Iddan |
| 2003/0208107 A1 | 11/2003 | Refael |
| 2004/0066262 A1 | 4/2004 | Wenner |
| 2004/0073087 A1 | 4/2004 | Glukhovsky et al. |
| 2004/0087832 A1 | 5/2004 | Glukhovsky et al. |
| 2004/0111011 A1 | 6/2004 | Uchiyama et al. |
| 2004/0115877 A1 | 6/2004 | Iddan |
| 2004/0138558 A1 | 7/2004 | Dunki-Jacobs et al. |
| 2004/0162501 A1 | 8/2004 | Imran |
| 2004/0176684 A1 | 9/2004 | Tabuchi et al. |
| 2004/0180391 A1 | 9/2004 | Gratzl et al. |
| 2004/0210105 A1 | 10/2004 | Hale et al. |
| 2004/0215068 A1 | 10/2004 | Lykke et al. |
| 2005/0110881 A1 | 5/2005 | Glukhovsky et al. |
| 2005/0148816 A1 | 7/2005 | Glukhovsky et al. |
| 2005/0171418 A1 | 8/2005 | Lin |
| 2005/0183733 A1 | 8/2005 | Kawano et al. |
| 2005/0288594 A1 | 12/2005 | Lewkowicz et al. |
| 2006/0061472 A1 | 3/2006 | Lovoi et al. |
| 2006/0136051 A1 | 6/2006 | Furst et al. |
| 2006/0155174 A1 | 7/2006 | Glukhovsky et al. |
| 2006/0164511 A1 | 7/2006 | Krupnik |
| 2006/0217593 A1 | 9/2006 | Gllad et al. |
| 2007/0106111 A1 | 5/2007 | Horn et al. |
| 2007/0225560 A1 | 9/2007 | Avni et al. |
| 2008/0103363 A1 | 5/2008 | Levy et al. |
| 2008/0269664 A1 | 10/2008 | Trovato et al. |
| 2008/0287833 A1* | 11/2008 | Semler et al. ............... 600/593 |
| 2009/0306632 A1 | 12/2009 | Trovato et al. |
| 2010/0121225 A1 | 5/2010 | Lewkowicz et al. |

FOREIGN PATENT DOCUMENTS

| | | |
|---|---|---|
| DE | 10121191 | 9/2002 |
| EP | 0344770 | 12/1989 |
| GB | 2 374149 | 9/2002 |
| JP | 55009033 | 1/1980 |
| JP | 57-45833 | 3/1982 |
| JP | 62-019857 | 5/1987 |
| JP | 01-305925 | 12/1989 |
| JP | 3-289779 | 12/1991 |
| JP | 4109927 | 4/1992 |

(56) References Cited

FOREIGN PATENT DOCUMENTS

| | | |
|---|---|---|
| JP | 04-138128 | 5/1992 |
| JP | 1992-144533 | 5/1992 |
| JP | 4-180736 | 6/1992 |
| JP | 5015515 | 1/1993 |
| JP | 6285044 | 10/1994 |
| JP | 07-111985 | 5/1995 |
| JP | 08-503384 | 4/1996 |
| JP | 2001224553 | 8/2001 |
| JP | 2002/508201 | 3/2002 |
| JP | 2002-186672 | 7/2002 |
| JP | 2003-038424 | 2/2003 |
| JP | 2004520410 | 7/2004 |
| WO | WO 88/00449 | 1/1988 |
| WO | WO 92/21307 | 10/1992 |
| WO | WO 94/01165 | 1/1994 |
| WO | WO 96/25877 | 8/1996 |
| WO | WO 98/11816 | 3/1998 |
| WO | WO 99/30610 | 6/1999 |
| WO | WO 99/61070 | 12/1999 |
| WO | WO 00/38655 | 7/2000 |
| WO | WO 01/08548 | 2/2001 |
| WO | WO 01/50941 | 7/2001 |
| WO | WO 01/65995 | 9/2001 |
| WO | WO 01/78836 | 10/2001 |
| WO | WO 01/87377 A2 | 11/2001 |
| WO | WO 02/058531 | 8/2002 |
| WO | WO 02/073507 | 9/2002 |
| WO | WO 02/082979 | 10/2002 |
| WO | WO 02/087493 | 11/2002 |
| WO | WO 02/095351 | 11/2002 |
| WO | WO 03/005877 | 1/2003 |
| WO | WO 03/005951 | 1/2003 |
| WO | WO 03/011103 | 2/2003 |
| WO | WO 03/094723 | 11/2003 |
| WO | WO 2004/004540 | 1/2004 |
| WO | WO 2004045395 | 6/2004 |
| WO | WO 2004/082472 | 9/2004 |

OTHER PUBLICATIONS

Lembo, Anthony, et. al., Chronic Constipation, New England Journal of Medicine, vol. 349, Oct. 2003, pp. 1360-1368, DOI: 10.1056/NEJMra020995. (http://www.nejm.org/doi/full/10.1056/NEJMra020995#t=article).*

Maqbool, Sabba, et. al., Wireless Capsule Motility: Comparison of the SmartPill® GI Monitoring System with Scintigraphy for Measuring Whole Gut Transit, Digestive Diseases and Sciences, vol. 54, Issue 10, Aug. 2009, pp. 2167-2174, DOI: 10.1007/s10620-009-0899-9. (http://link.springer.com/article/10.1007/s10620-009-0899-9#).*

Roberts, Mr JP. "Oral [111In] DTPA scintigraphic assessment of colonic transit in constipated subjects." Digestive diseases and sciences 38.6 (1993): 1032-1039. (http://link.springer.com/article/10.1007/BF01295718).*

Maurer, Alan H., and Henry P. Parkman. "Update on gastrointestinal scintigraphy." Seminars in nuclear medicine. vol. 36. No. 2. WB Saunders, 2006.*

The Radio Pill, Rowlands, et al., British Communications and Electronics, Aug. 1960, pp. 598-601.

Wellesley company sends body monitors into space, Boston Business Journal, Crum, Apr. 1998.

Wireless transmission of a colour television moving image from the stomach using a miniature CCD camera, light source and microwave transmitter. Swain CP, Gong F, Mills TN. American Society of GastrointestinalEndoscopy, Apr. 1997; vol. 45: AB40.

BBC News Online, Pill camera to 'broadcast from the gut,' Feb. 21, 2000, www.news.bbc.co.uk.

W. Weitschies, R. Kotitz, D. Cordini, L. Trahms, High-Resolution Monitoring of Gastrointestinal Transit of Magnetically Marked Capsule, (1997), Journal of Pharmaceutical Sciences, vol. 86, No. 11, pp. 1218-1222.

Transit times for the Capsule Endoscope, American Society of Gastrointestinal Endoscopy, 2001: vol. 53, AB122.

International Search Report for International Application No. PCT/IL02/00562, dated Apr. 21, 2008.

European Search report of Application No. EP 05077574.1, dated Jun. 30, 2006.

Supplementary Partial European Search Report for European Patent Application No. 02745775.3 dated Jan. 20, 2011.

Office Action for Japanese Patent Application No. 2005-323164, dated Mar. 8, 2011.

Office Action for European Patent Application No. 02745775.3, dated May 17, 2011.

Supplementary European Search Report for Application No. EP 03 77 8736.3, dated Apr. 21, 2008.

International Search Report for International Application No: PCT/IL03/01080, mailed Aug. 23, 2004.

Office Action for European Application No. 03778736.3, Dated May 12, 2009.

Office Action for European Application No. 03778736.3, Dated Jan. 11, 2012.

Office Action for European Application No. 03778736.3, Dated Nov. 29, 2010.

"Biomedical Telemetry". R Stewart McKay. John Wiley and Sons, 1970. p. 244~245.

Roubik, et al., "Reference Microelectrodes Design Evaluation for On-Chip ISFET-Based Microsensors for 'In vivo' Blood Measurements," 2000.

Wang, et al. "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uklNaa.publications.html.

U.S. Appl. No. 60/457,592, filed Mar. 27, 2003, Iddan.

F. Vald's-Perezgasga, et al., "Isfet Applications in Biological Matter: An Overview", downloaded Oct. 27. 2002, www.cinstrum.unnm.mxlrevistnlpdfv4n3/art3.PDF.

Shin-ichi, et al , "Robots for the future", NIPPONIA, Nov. 29, 2001.

"Video Camera to Take" RF System lab, Dec. 25, 2001.

—NORIKA3, www.rfnorika.com, Dec. 24, 2001.

* cited by examiner

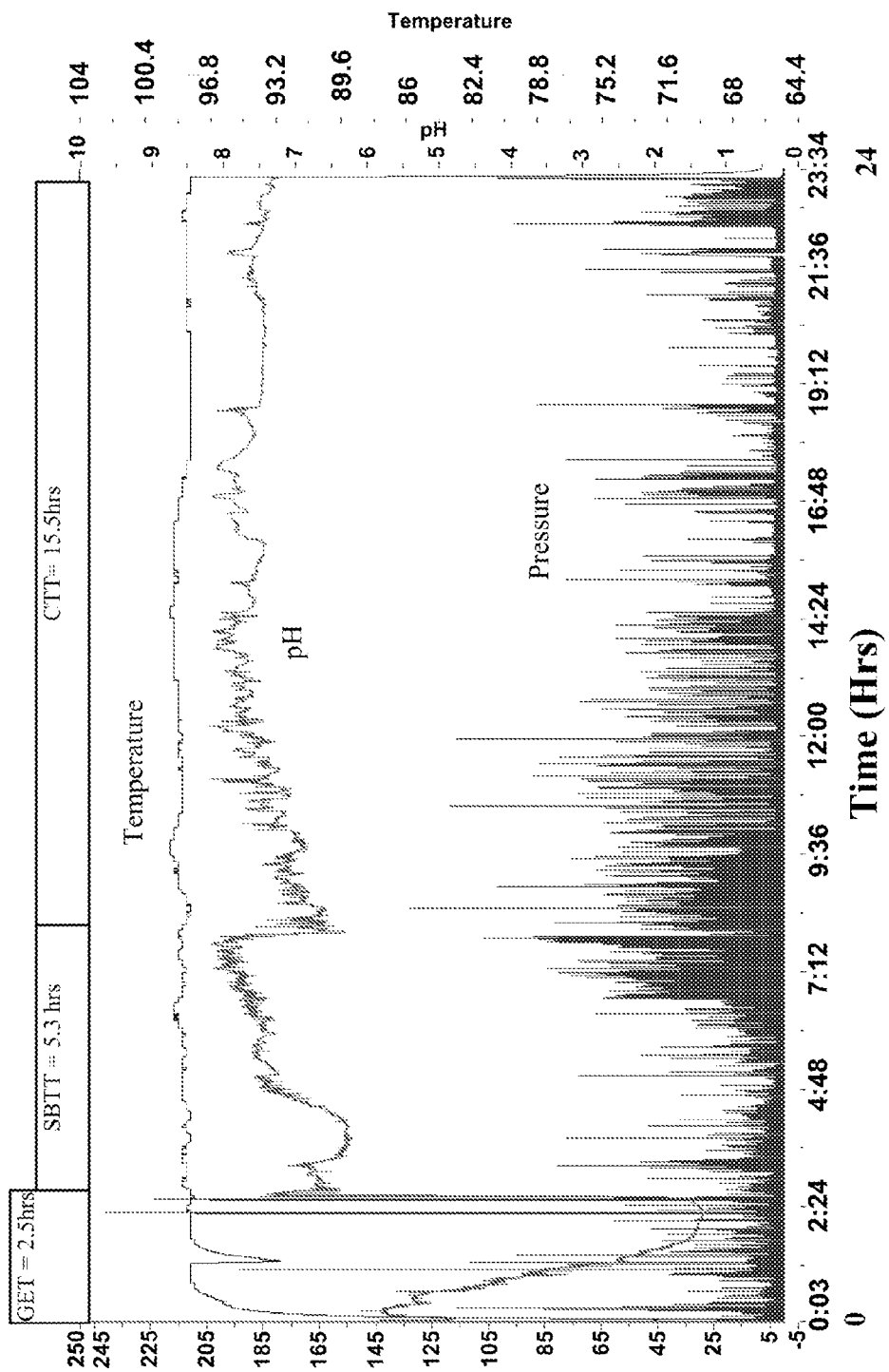
FIG. 8A: Example of the capsule system and ROMs recording in a healthy subject. The healthy subject shows normal GET at 2.5 hours, normal SBTT at 5.3 hours, and normal CTT at 15.5 hours, and 4 ROMs on the day 2 radiograph.

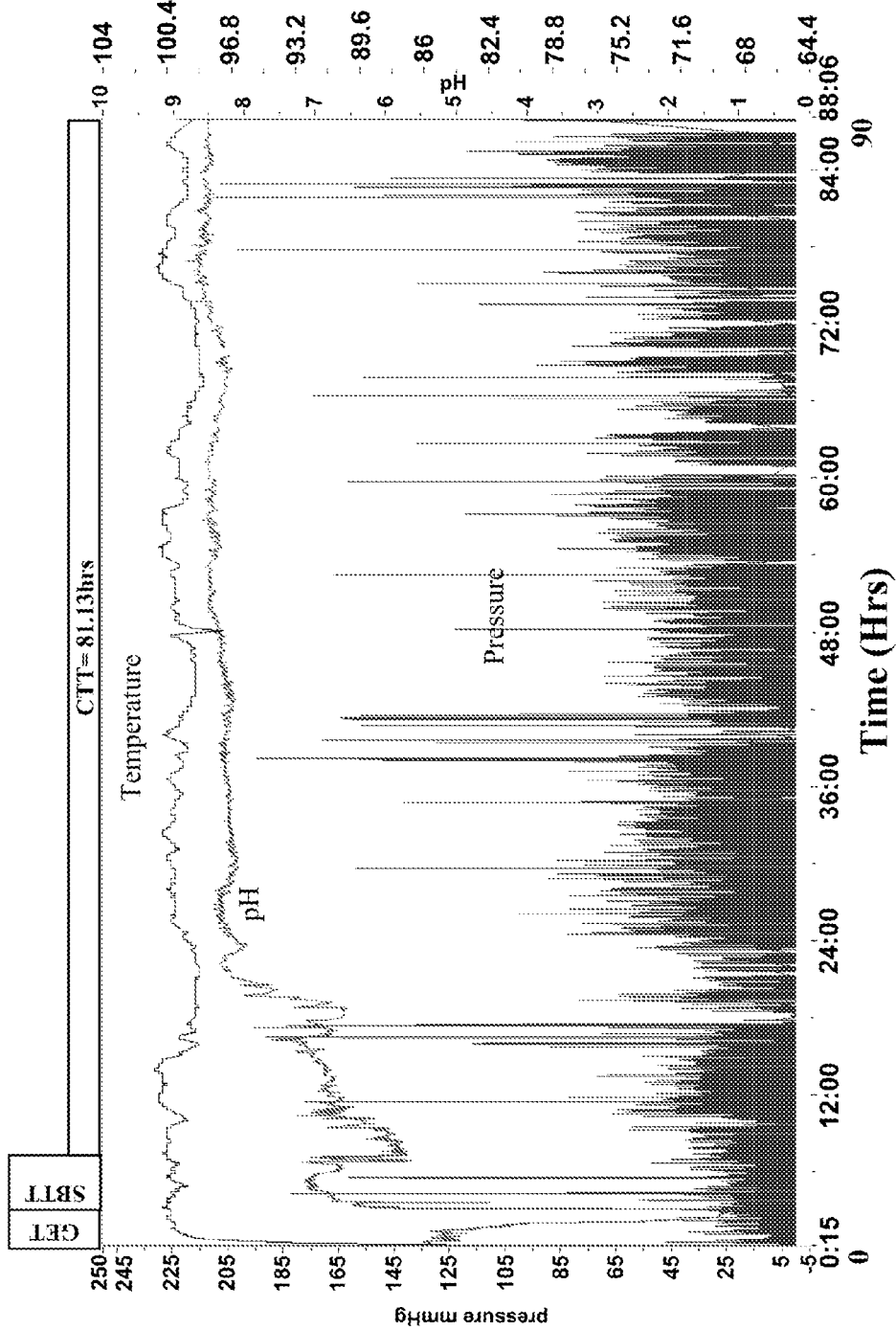
FIG. 8B: Example of the capsule system and ROMs recording in a constipated subject. The constipated subject shows a normal GET at 2.88 hours, normal SBTT at 3.58 hours, and delayed CTT at 81.13 hours. The day 2 radiograph shows the capsule and 24 ROMs and the day 5 radiograph shows that the capsule has been expelled but 10 ROMs remain.

Box-and-whisker plots for capsule derived CTT in healthy and constipated subject, and effects of sex. CTT was significantly slower in constipated women and men compared with controls.

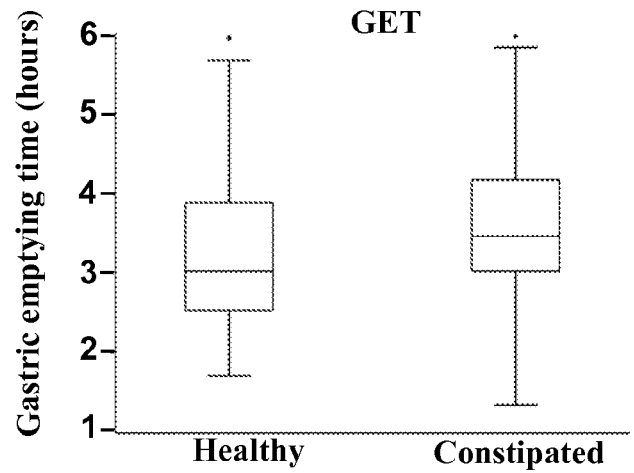
FIG. 10A: Box-and-whisker plot for GET.
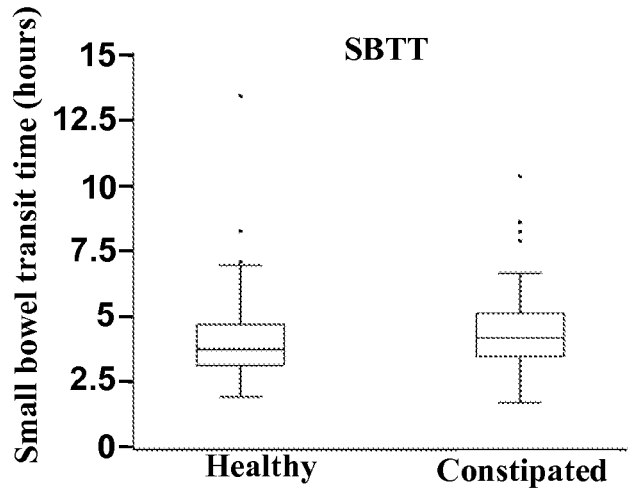
FIG. 10B: Box-and-whisker plot for SBTT.
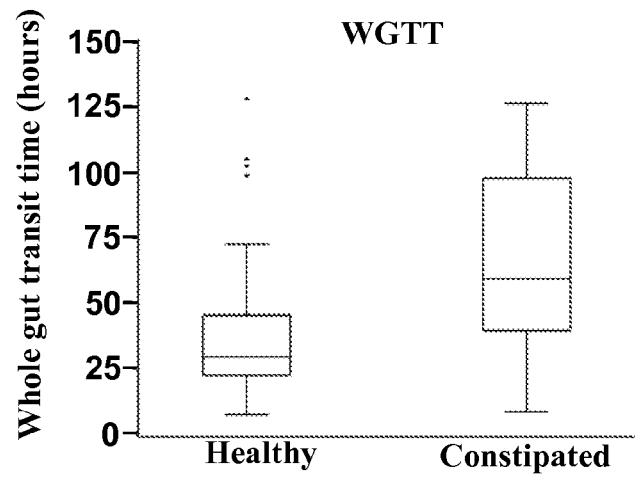
FIG. 10C: Box-and-whisker plot for WGTT.

METHOD OF EVALUATING CONSTIPATION USING AN INGESTIBLE CAPSULE

CROSS-REFERENCE TO RELATED APPLICATIONS

This application claims the benefit of U.S. Provisional Patent Application No. 61/289,867, filed Dec. 23, 2009. The entire content of such application is incorporated by reference herein.

TECHNICAL FIELD

The present invention relates generally to ingestible capsules and, more particularly, to a process for evaluating a subject for constipation with an ingested capsule passing through the digestive tract of the subject.

BACKGROUND ART

Ingestible capsules are well-known in the prior art. Such capsules are generally small pill-like devices that can be ingested or swallowed by a patient. It is known that such capsules may include one or more sensors for determining physiological parameters of the gastrointestinal tract, such as sensors for detecting temperature, pH and pressure.

It is also known that certain physiological parameters may be associated with regions of the gastrointestinal tract. For example, a 1988 article entitled "Measurement of Gastrointestinal pH Profiles in Normal Ambulant Human Subjects" discloses pH measurements recorded by a capsule passing through the gastrointestinal tract. It is known that pH has been correlated with transitions from the stomach to the small bowel (gastric emptying) and from the distal small bowel to the colon (ileo-caecal junction).

Constipation is a common disorder of the gastrointestinal tract. In clinical practice, constipation is defined by symptoms rather than specific abnormalities in physiology and patients with constipation exhibit a wide variety of symptoms. This diversity in clinical presentation is reflected in the symptom-based diagnostic criteria offered by the Rome Foundation's Third International Congress meeting (Rome III), as well as the American College of Gastroenterology's Functional GI Disorders Task Force. A number of different physiological abnormalities have been implicated in chronic constipation. These include delayed colonic transit (STC), the inability to coordinate the series of events necessary to allow the normal evacuation (DD), and physical obstructions. STC and DD are the most frequently observed physiological abnormalities in chronic constipation. Studies from secondary and tertiary care centers have found the prevalence of STC to vary 15-45% in constipated patients while up to 59% have DD. STC and DD can coexist in the same patient. Additionally 50% of patients routinely have normal results on physiological testing while meeting the symptom criteria for chronic constipation.

Although Rome III criteria help in the evaluation of patients with chronic constipation, they are not precise predictors of underlying pathophysiology, nor do they provide a reliable guide to patient management or predict upper gut involvement where the lack of appropriate diagnosis may lead to poor management of patients with concomitant upper gut disorders.

A systematic review of tests that are commonly used in the evaluation of constipation concluded that whole gut and colonic transit measurements, anorectal manometry and balloon expulsion tests are complementary and can be helpful in the management of patients with constipation. Colonic transit studies aid in the differentiation between slow and normal transit constipation, an important distinction for facilitating treatment selection and patient management. When whole gut or colonic transit is delayed, a prokinetic treatment may be indicated. However, when transit is normal and visceral hypersensitivity may be present, treatment with low dose tricyclic antidepressants or visceral analgesics may be indicated. Further, recent evidence suggests that many patients with chronic constipation also have abnormalities in motor function and transit of the stomach and/or small intestine. Such findings break with the conventional wisdom which states that constipation results from physiological abnormalities confined to the colon and pelvic floor. Rather, these findings suggest that a more diffuse abnormality in gastrointestinal motility and transit is present in a substantial proportion of constipation sufferers. As such, the functional evaluation of the entire gastrointestinal tract is valuable in patients with severe chronic constipation.

Numerous published studies describe the assessment of colonic transit using radiopaque marker (ROM) techniques in patients with constipation. The prevalence of slow and normal transit constipation as defined by ROM vary considerably from study to study. Variability most likely results from differences in severity of the condition in the population studied, differences in the ROM criteria used to define normality, and inherent variability in colonic transit.

The standard ROM method used clinically produces dichotomous results. Six or more markers remaining on day 5 suggests transit delay, whereas 5 or fewer remaining suggests normal transit. Other ROM methods used clinically are based on the Metcalf protocol, involve multiple marker ingestions, and the number of markers remaining at day 4 equated to transit time in hours.

Although widely used, the ROM test has intrinsic drawbacks that include radiation exposure, inability to assess regional gut transit, and lack of standardized protocols for the test and its interpretation. Also, some protocols require multiple visits, which affects compliance.

Scintigraphy has been validated for the evaluation of regional and whole gut transit, but is expensive, involves radiation and is not widely available. Consequently, most centers use multiple techniques to assess regional gut transit such as gastric emptying with scintigraphy, small bowel transit with radio-labeled meal or lactulose breath test, and colonic transit time with ROM, which is a time consuming and expensive approach.

BRIEF SUMMARY OF THE INVENTION

With parenthetical reference to corresponding parts, portions or surfaces of the disclosed embodiment, merely for the purposes of illustration and not by way of limitation, the present invention provides an improved method for diagnosing constipation comprising the steps of providing an ingestible capsule (20) having a given density and/or size and a pH sensor (22) and a temperature sensor (24), having a subject ingest the capsule, recording pH measurements from the pH sensor as a function of time as the capsule moves through at least a portion of the gastrointestinal tract of the subject, transmitting the pH measurements to a processor (31) outside of the gastrointestinal tract of the subject, recording temperature measurements from the temperature sensor as a function of time as the capsule moves through at least a portion of the gastrointestinal tract of the subject, transmitting the temperature measurements to a processor (31) outside of the gastrointestinal tract of the subject, determining transit time of the capsule between a first location in the gastrointestinal tract of the subject and a second location in the gastrointestinal tract of the subject as a function of the pH measurements and the temperature measurements, providing a reference transit time, and comparing the determined transit time to the reference transit time to evaluate the subject for constipation.

The first position may be the junction between the stomach and the small bowel of the gastrointestinal tract of the subject. The second position may be the junction between the ileum and caecum of the gastrointestinal tract of the subject. The first position may be the junction between the ileum and the caecum of the gastrointestinal tract of the subject and the second position may be the end of the gastrointestinal tract of the subject. The step of comparing the transit time to the reference transit time may comprise the step of determining whether the transit time is greater than or less than the reference transit time. The method may further comprise the steps of providing the ingestible capsule with a pressure sensor, recording pressure measurements from the pressure sensor as a function of time as the capsule moves through at least a portion of the gastrointestinal tract of the subject, transmitting the pressure measurements to the processor outside of the gastrointestinal tract of the subject, and determining the transit time between the first position and the second position as a function of the pressure measurements. The transit time may be gastric emptying time, small bowel transit time, colonic transit time, small and large bowel transit time and/or whole gut transit time. The reference transit time may be a function of capsule density and/or size.

Accordingly, the general object is to provide a method for evaluating a subject for constipation using an ingested capsule.

Another object is to provide a method of evaluating constipation in a non-invasive manner suitable for the office setting.

These and other objects and advantages will become apparent from the foregoing and ongoing written specification, the drawings, and the claims.

BRIEF DESCRIPTION OF THE DRAWINGS

FIGS. 8A and 8B show a graph of pressure, pH and temperature versus time in a healthy (A) and a constipated (B) subject. The healthy subject showed normal GET at 2.5 hours, normal SBTT at 5.3 hours, and normal CTT at 15.5 hours, and a corresponding ROM showed 4 ROMs on the day 2 radiograph. The constipated subject showed a delayed GET at 5.8 hours, normal SBTT at 4.3 hours, and delayed CTT at 80.25 hours. The day 2 radiograph showed the capsule and 24 ROMs and the day 5 radiograph showed the capsule had been expelled but 10 ROMs remained.

FIGS. 10A, 10B and 10C are box-and-whisker plots for GET (A), SBTT (B) and WGTT (C). GET and WGTT were slower in constipated subjects.

DESCRIPTION OF THE PREFERRED EMBODIMENTS

Figure 1:
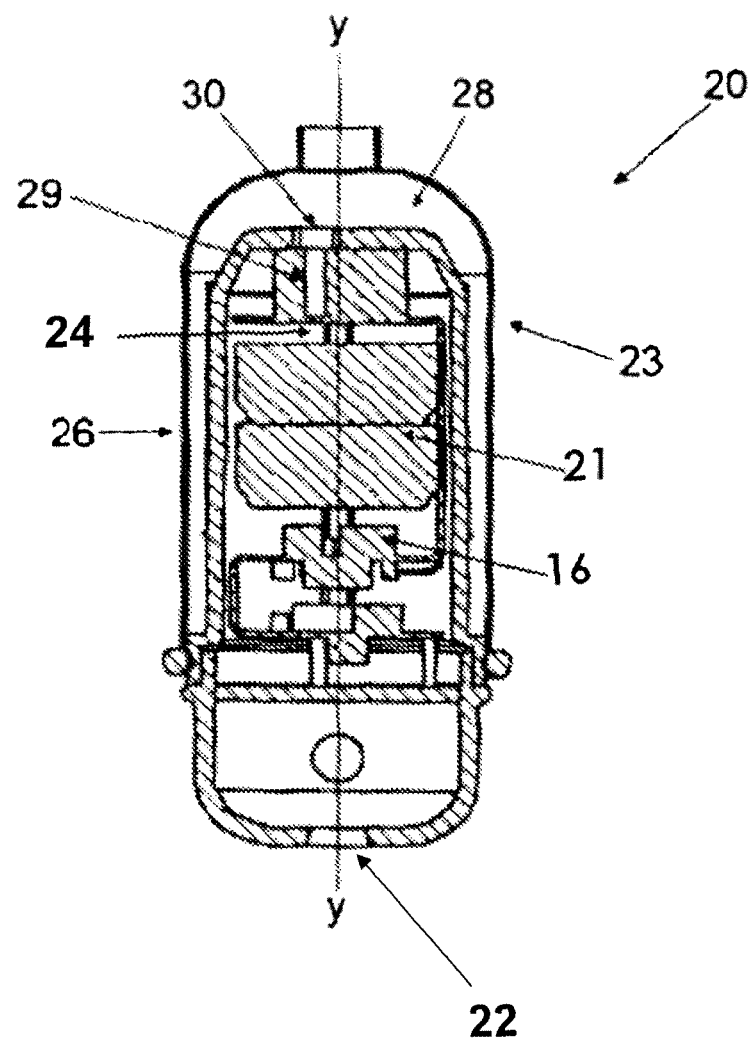
FIG. 1 is a sectional view of an embodiment of an ingestible capsule adapted to record pressure, pH and temperature measurements in the gastrointestinal tract.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

A method is provided for evaluating a subject for constipation using an ingestible capsule as a function of pH readings taken by the ingested capsule, density and/or size of the ingested capsule and transit times. Capsule 20 is ingested by a subject and readings from sensors on the capsule are taken as the capsule passes through the gastrointestinal tract of the subject. Data from pressure sensor 23, pH sensor 22 and temperature sensor 24 are collected and analyzed to determine transit times, which are compared to one or more reference templates or criteria for the density and/or size of capsule 20 to evaluate the subject for constipation.

Figure 2:
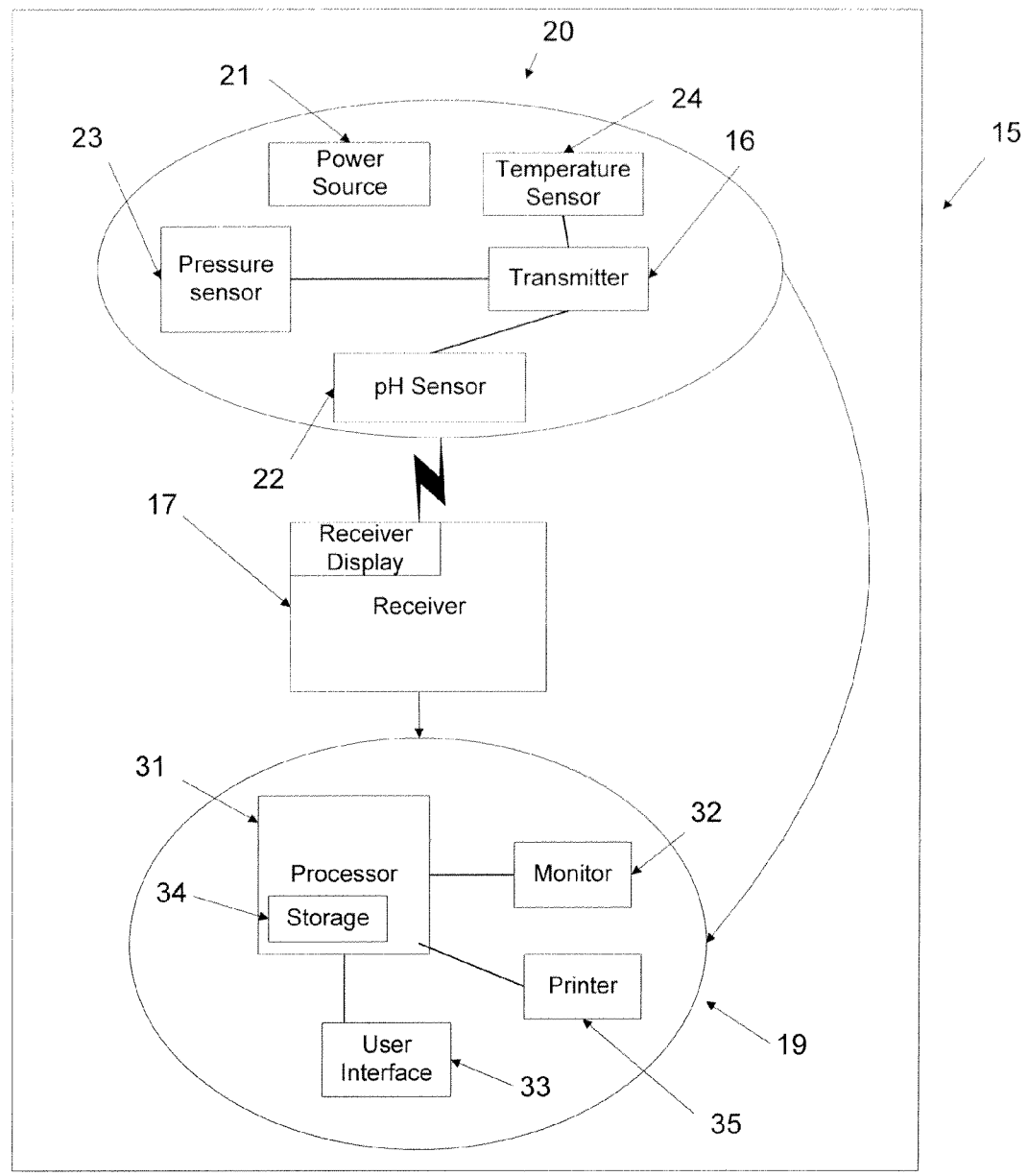
FIG. 2 is a schematic of an embodiment of a capsule system for evaluating a subject for constipation.

Referring now to the drawings, and more particularly to FIG. 2 thereof, this invention provides a new method for evaluating constipation using an ingested capsule system, of which a first embodiment is generally indicated at 15. As shown in FIG. 2, capsule system 15 generally includes ingestible capsule 20, receiver 17, and computer workstation 19. Capsule 20 includes pressure sensor assembly 23, pH sensor 22 and temperature sensor 24 for taking measurements of pressure, pH and temperature, respectively, of a subject's gastrointestinal tract, power source 21, and transmitter 16 for transmitting the measurement data. Receiver 17 is configured to receive signals sent from transmitter 16. Computer workstation 19 includes processor 31 and is programmed to process measurements from pressure sensor 23, pH sensor 22 and temperature sensor 24.

As shown in FIG. 1, capsule 20 is generally a cylindrical member elongated about axis y-y and having generally rounded closed ends, somewhat resembling a medicament capsule. The capsule generally has a hard shell or casing which houses the transmitting electronics, a battery compartment, power supply 21, transmitter 16, an antenna, an activation switch, pressure sensor assembly 23, pH sensor 22 and temperature sensor 24. Capsule 20 is adapted to be ingested or otherwise positioned within a tract to sense pressure, pH and temperature within the tract and to transmit such readings to receiver 17. Capsule 20 is generally provided with an outer surface to facilitate easy swallowing of the capsule and is an autonomous swallowable capsule that is self-contained. Thus, capsule 20 does not require any wires or cables to, for example, receive power or transmit information. The pressure, pH and/or temperature data is transmitted from capsule 20 within the gastrointestinal tract to remote data receiver 17.

Pressure sensor assembly 23 comprises a chamber 28 between an inner wall and a flexible sleeve 26 of the capsule. The chamber 28 is filled with a fluid. A rigid PCB arm extends to the chamber and supports a conventional piezoelectric bridge. Sensing mechanism 29 is operatively arranged to communicate with chamber 28 through fluid port 30 at one end of the shell of capsule 20. As fluid presses against the bridge, it creates an electrical signal which corresponds to the pressure of fluid in chamber 28. The fluid is a non-compressible medium that forms part of the 360° degree force sensing mechanism for the sensor. In the preferred embodiment, the fluid used is mineral oil. Alternatively, it is contemplated that an inert gas may be used instead of a fluid. Thus, pressure sensor 23 is operatively arranged to sense pressure within chamber 28.

In this embodiment, power supply 21 is a lithium battery, although it is contemplated that other batteries may be used, such as a silver-oxide battery. Power supply 21 is adapted to power the electrical components of capsule 20 when in the gastrointestinal tract of a subject. To maximize its operational life, battery 21 is activated just prior to ingestion by way of an activation switch adapted to turn the capsule on and off. In this embodiment, the activation switch is a circuit operating between battery 21 and the electrical components that selectively powers on and off the electronic components by way of a magnetic sensor which responds selectively to the presence, absence and/or polarity of a magnetic field. A number of conventional switches may be used. For example, an "active" reed switch system may be used, in which an external magnetic field actively holds a reed switch so that the circuit remains open. When the ingestible capsule is removed from the magnetic field, the reed switch closes the circuit, thereby activating the capsule. An alternative method is to use a passive reed switch and a magnetizable bias magnet asymmetric design manipulated by an external magnet. The circuitry of the capsule is selectively switched on and off depending on the magnetic state of the bias magnet, which determines the reed switch on/off state.

In this embodiment, transmitter 16 is a radio frequency (RF) transmitter that transmits measurements from the capsule when it is in the gastrointestinal tract of a subject to remote receiver 17. Transmitter 16 transmits measurements at about 434 MHz. Portable data receiver 17 worn by the subject receives and stores the measurements transmitted by transmitter 16 for later download through a docking station to computer 19. An antenna amplifies the transmit power of transmitter 16 so that it can be received by remote receiver 17.

Capsule 20 includes a conventional temperature sensor 24. Besides being used in determining body exit, temperature sensor 24 may also be used to compensate or provide a baseline relative to the other sensors in capsule 20.

On the opposite end of capsule 20 to pressure sensor 23 is pH sensor 22. In this embodiment, pH sensor 22 comprises a conventional ISFET type pH sensor. ISFET stands for ion-selective field effect transistor and the sensor is derived from MOSFET technology (metal oxide screen field effect transistor). A current between a source and a drain is controlled by a gate voltage. The gate is composed of a special chemical layer which is sensitive to free hydrogen ions (pH). Versions of this layer have been developed using aluminum oxide, silicon nitride and titanium oxide. Free hydrogen ions influence the voltage between the gate and the source. The effect on the drain current is based solely on electrostatic effects, so the hydrogen ions do not need to migrate through the pH sensitive layer. This allows equilibrium, and thus pH measurement, to be achieved in a matter of seconds. The sensor is an entirely solid state sensor, unlike glass bulb sensors which require a bulb filled with buffer solution. Only the gate surface is exposed to the sample.

In this embodiment, capsule 20 transmits sensed data at about 434 MHz, measures about 26.8 mm long by about 11.7 mm in diameter, has an average volume of about 141.2 cm$^3$ and a density in the range of about 0.026 to about 0.029 grams per cm$^3$.

After activation and ingestion, capsule 20 senses and transmits data for at least 120 hours after activation. The pH, pressure and temperature data are transmitted from within the GI tract to data receiver 17. In the preferred embodiment, the range and accuracy of the sensors are generally 0.5 to 9.0 pH units with an accuracy of ±0.5 pH units, 0 to 350 mmHg with an accuracy of 5 mmHg, or 10% above 100 mmHg, and 25° to 49° C. with an accuracy of ±1° C.

Capsule 20 is provided to the subject and ingested by the subject. Readings are then taken from sensors 22, 23, and 24 on capsule 20 as it passes through the gastrointestinal tract of the subject. Raw data measurements from pH sensor 22, pressure sensor 23, and temperature sensor 24 are transmitted in data packets from transmitter 16 to data receiver 17, which is outside the body of the subject. Portable data receiver 17 worn by the subject receives and stores the data packets transmitted by capsule 20. After data recording is complete, data receiver 17 is placed into a docking station. Data receiver 17 contains rechargeable batteries and when seated in a docking station allows for battery charging and data download. Data is downloaded from data receiver 17 through the docking station via a USB connection to Windows PC compatible computer 19. In this embodiment, computer 19 is a conventional laptop or desktop computer.

In this embodiment, computer 19 includes a processor 31, data processing storage 34, a monitor or display 32, a user input device 33 and printer 35. In this embodiment, monitor 32 is a computer screen. However, monitor 32 may be any other device capable of displaying an image or other data. In this embodiment, user input device 33 includes a keyboard and a mouse. However, user input device 33 could be any other suitable input-output device for interfacing with data processor 31.

The processing and analysis of the pressure, pH and temperature from capsule 20 is generally provided using computer-executable instructions executed by a general-purpose computer, such as a server or personal computer 19. However, it should be noted that this processing and analysis may be practiced with other computer system configurations, including internet appliances, hand-held devices, wearable computers, multi-processor systems, programmable consumer electronics, network PCs, mainframe computers and the like. The term computer or processor as used herein refers to any of the above devices as well as any other data processor. Some examples of processors are microprocessors, microcontrollers, CPUs, PICs, PLCs, PCs or microcomputers. A computer-readable medium comprises a medium configured to store or transport computer readable code, or in which computer readable code may be embedded. Some examples of computer-readable media are CD-ROM disks, ROM cards, floppy disks, flash ROMS, RAM, nonvolatile ROM, magnetic tapes, computer hard drives, conventional hard disks, and servers on a network. The computer systems described above are for purposes of example only. An embodiment of the invention may be implemented in any type of computer system or programming or processing environment. In addition, it is meant to encompass processing that is performed in a distributed computing environment, were tasks or modules are performed by more than one processing device or by remote processing devices that are run through a communications network, such as a local area network, a wide area network or the internet. Thus, the term processor is to be interpreted expansively.

Computer 19 is programmed to extract information from the pressure measurements taken by pressure sensor 23, the pH measurements taken by pH sensor 22, and the temperature measurements taken by temperature sensor 24, and to use that data to make a determination regarding the subject. The analysis and evaluation is displayed in graphical form on monitor 32 for the user.

Raw data measurements are conditioned by computer 19 through the removal of invalid packets, conversion of the data into proper units and the scaling of pressure to ambient. The invalid packets are screened using a conventional packet validation process. The temperature and pressure measurements are respectively converted into units of degrees Celsius and millimeters of mercury. The data is next analyzed by computer 19 and used to evaluate the subject for constipation. This determination is a function of a number of different variables.

In general, gastric emptying time (GET) is the time interval between ingestion of capsule and, in this embodiment, the time of an abrupt rise in pH profile, usually >2 pH units from the gastric pH baseline. This change occurs when the capsule passes from the acidic antrum to the alkaline duodenum. Small bowel transit time (SBTT) is the time interval between capsule entry into the small bowel and its entry into the caecum. In this embodiment, the cecal entry is identified by a distinct drop in pH of ≥0.5 pH units that is sustained for ≥10 minutes and occurs at least 30 minutes after capsule entry into the small bowel. This pH change is believed to occur in the cecum and is secondary to fermentation of digestive residue by colonic flora. Colonic transit time (CTT) is the time interval between the point of entry into the cecum and the capsule exit from the body. In this embodiment, body exit time (BET) is verified by a loss of signal and/or abrupt drop in temperature. Small and large bowel transit time (SLBTT) is the time interval between gastric emptying and body exit of the capsule. Whole gut transit time (WGTT) is the time interval between capsule ingestion and body exit.

Figure 3:
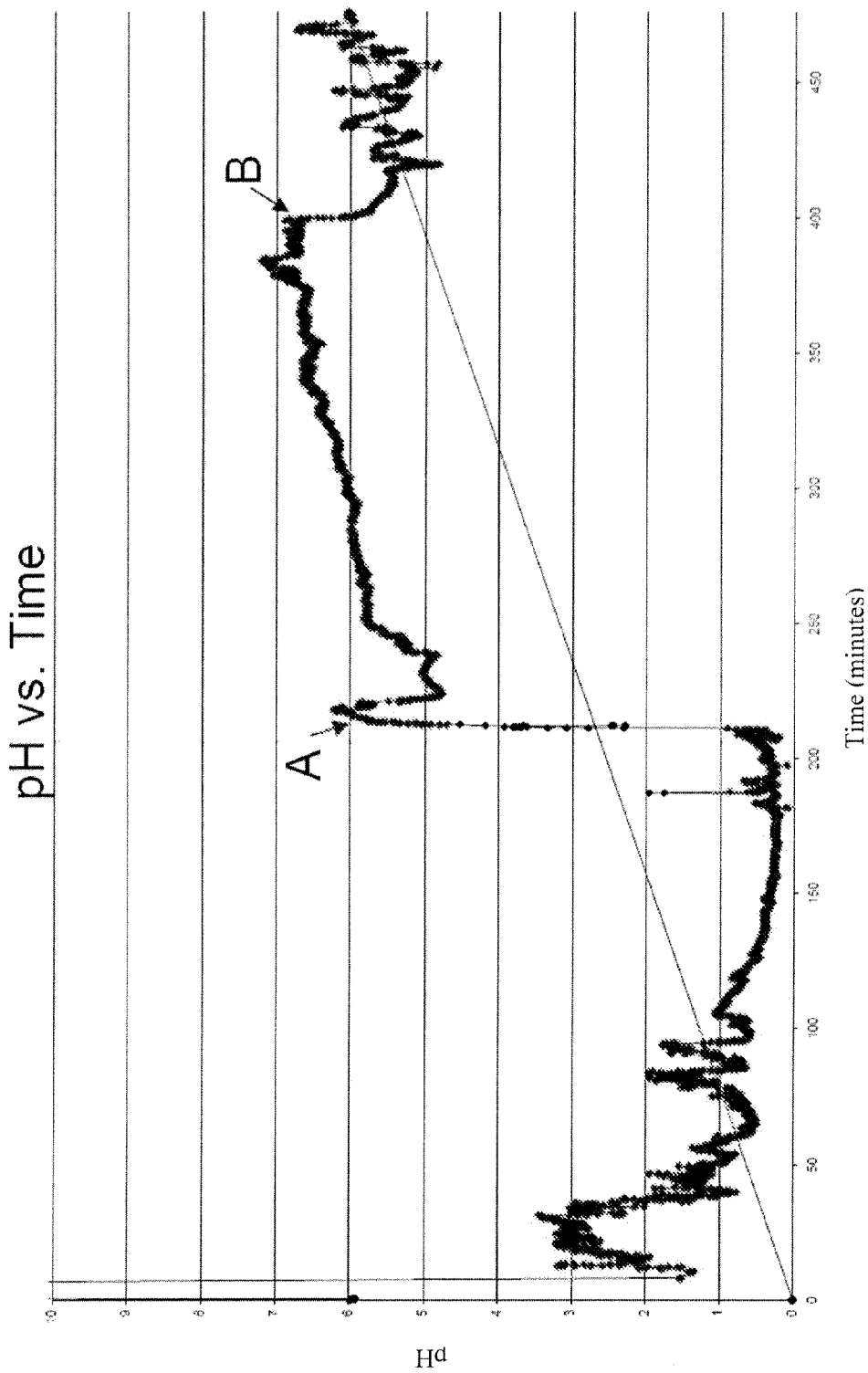
FIG. 3 is a graph of pH versus time taken by a capsule passing through the gastrointestinal tract.

In this embodiment, pH readings from the ingested capsule are plotted against time, as shown in FIG. 3. Based on reference data, a substantial variation or increase in pH, generally indicated at A, indicates passage of the capsule from the acidic antrum to the alkaline duodenum. Thus, based on the pH measurements taken by the capsule, its transition from the stomach to the small bowel can be determined as a function of time. The elapsed time from ingestion to this transition is calculated. In this embodiment, this location is marked as the point at which the pH abruptly rises more than 2 pH units from baseline pH to a pH of greater than 4. As described above, based on this determination, the capsules gastric emptying or residence time is determined. GET of the capsule is the duration of time from the capsule's ingestion to the point at which the foregoing pH rise is determined.

As described above, a latter variation in pH, indicated at B in FIG. 3, suggests movement of the capsule from the ileum to the caecum. It has been found that this significant pH drop is seen hours after gastric emptying and is due to the capsule moving from the ileum to the caecum, a transition referred to as the ileo-caecal junction. Thus, SBTT is determined from the time interval between capsule entry into the small bowel or GET and its entry into the caecum.

Figure 4:
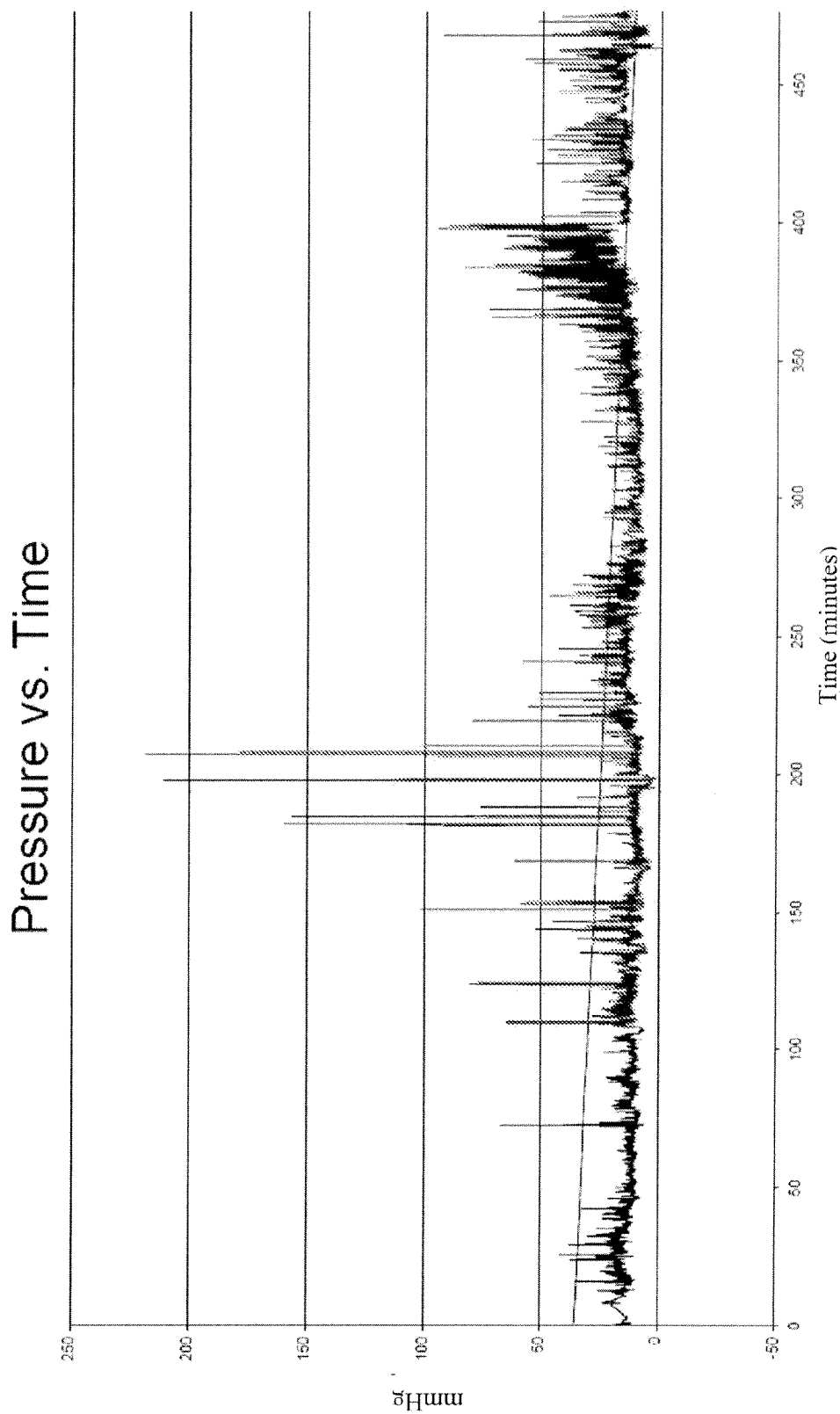
FIG. 4 is a graph of pressure over the same period of time shown in FIG. 3 taken by the capsule.
Figure 5:
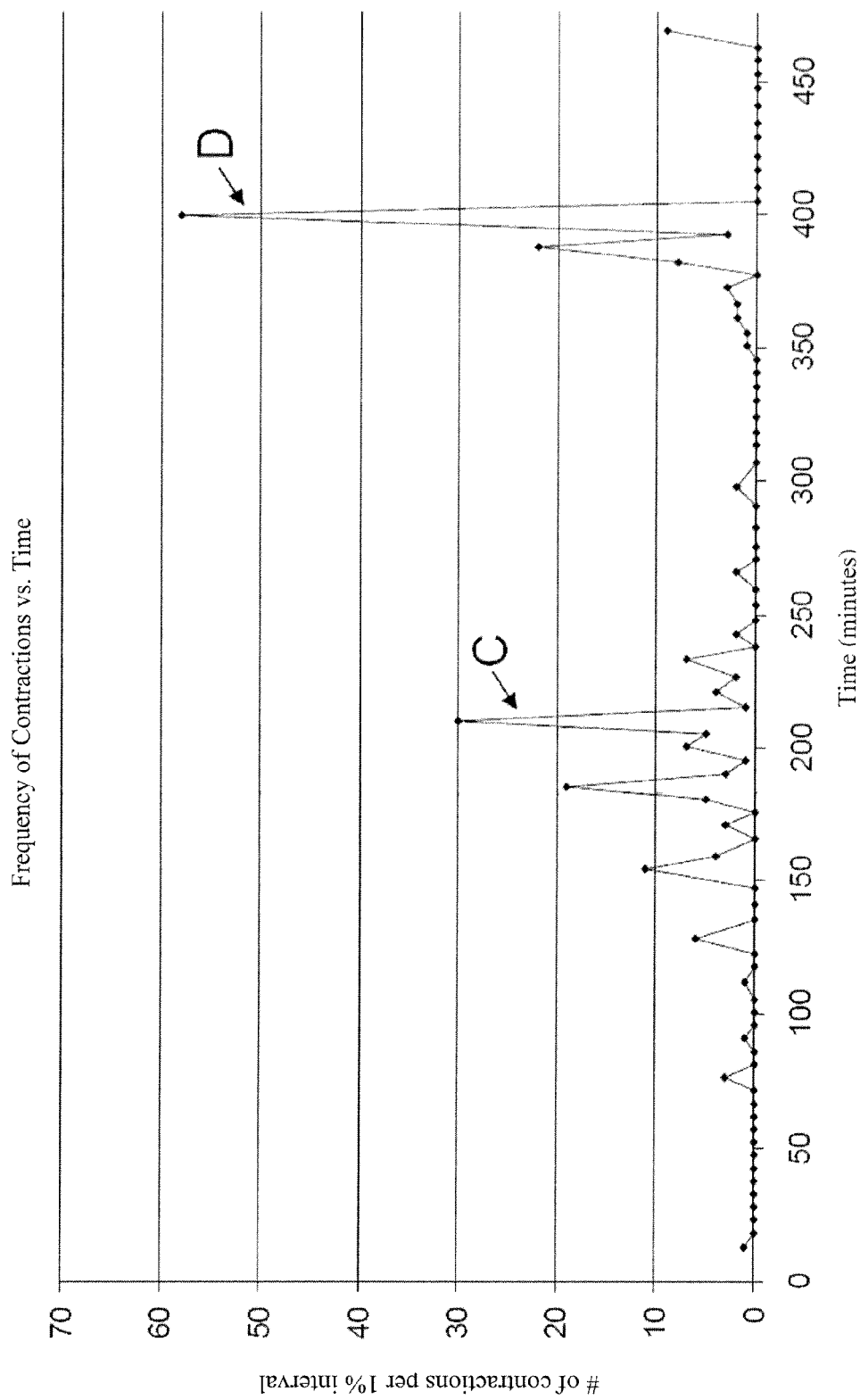
FIG. 5 is a graph of the number of contractions during five minute intervals over the same period of time shown in FIG. 4.

It is contemplated that not only may a variation in pH be used to determine the times that capsule 20 passes from the stomach and then passes the ileo-caecal junction, but an associated change in pressure pattern may also be employed. Average pressure readings from the capsule plotted against time are shown in FIG. 4. The number of contractions over a given time interval, five minutes in the preferred embodiment, plotted against the same overall time period, are shown in FIG. 5. In the preferred embodiment, a contraction is designated by an increase in pressure over 10 mmHg and the subsequent return below 10 mmHg. However, it is contemplated that gastrointestinal contractions may be determined based on other variations in pressure or baselines other than 10 mmHg. As shown in FIG. 5, a variation in the frequency of contractions is generally found to occur, as indicated at C, at a time corresponding to the gastric emptying suggested by the graph of pH shown in FIG. 3. This correlation between the variation in frequency of contractions at C and the variation in pH at A may be used as a reference to confirm GET.

Figure 6:
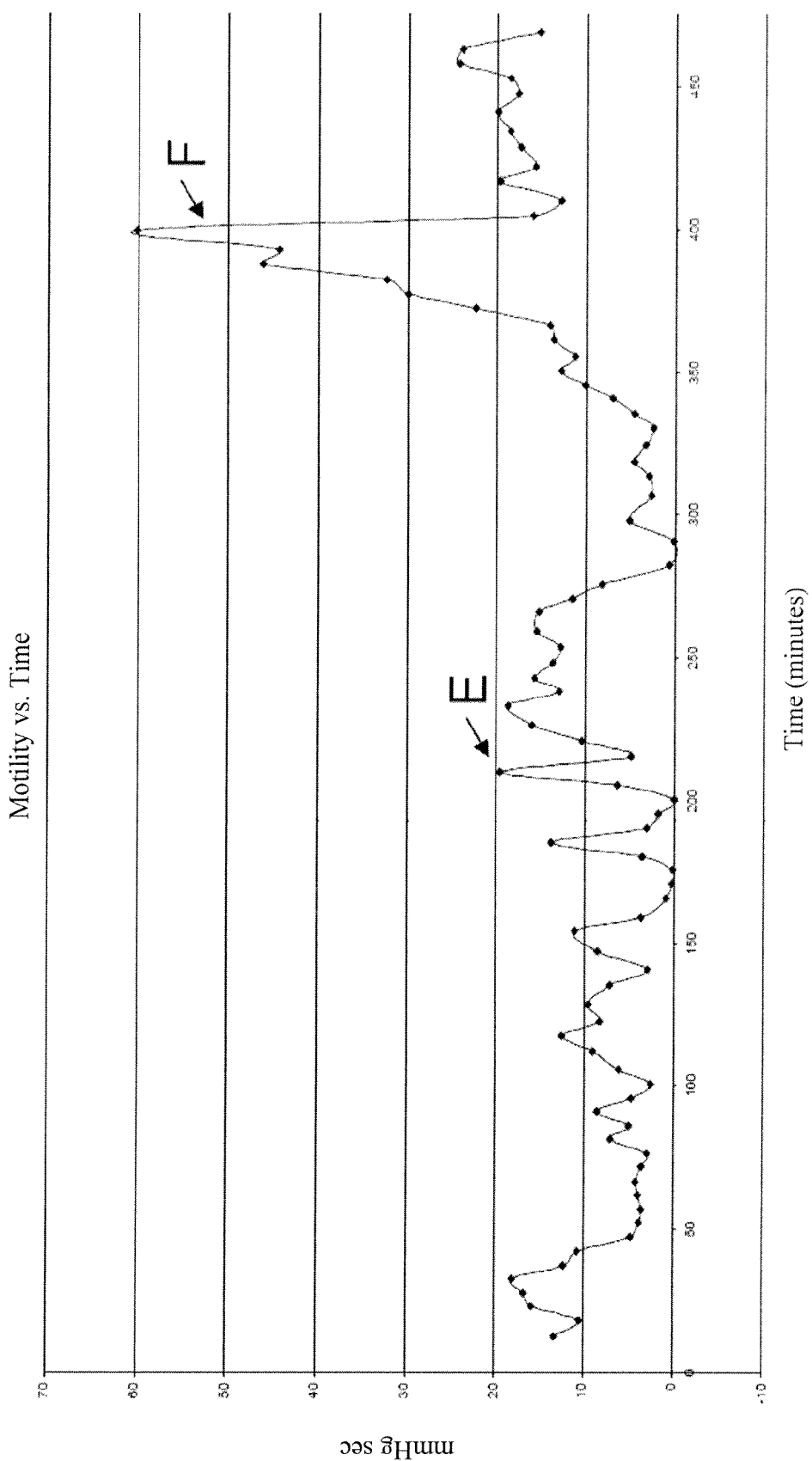
FIG. 6 is a graph of the normalized relative motility index for five minute intervals over the same period of time shown in FIG. 4.

A further and more substantial variation in frequency of contractions occurs, as indicated at D, at a time corresponding to the ileo-caecal junction suggested by the graph of pH shown in FIG. 3. FIG. 6 is a plot of the normalized relative motility index at five minute intervals versus time. Each data point is the area under the curve of the graph of pressure shown in FIG. 6 for five minute intervals. Motility index as used herein is the area under the curve (or the integral of pressure over a time region) divided by the size of the time region. While a five minute time region is used in this graph, other time periods may be employed. Plotted against transit time, generally a substantial variation occurs, indicated at F, at substantially the same time as the variation B in pH. This variation in motility index may also be used as a reference to confirm that the capsule has moved from the ileum to the caecum of the subject. This correlation between the variation in motility index at F and the variation in pH at B may therefore be used as a reference to determine SBTT.

Figure 7:
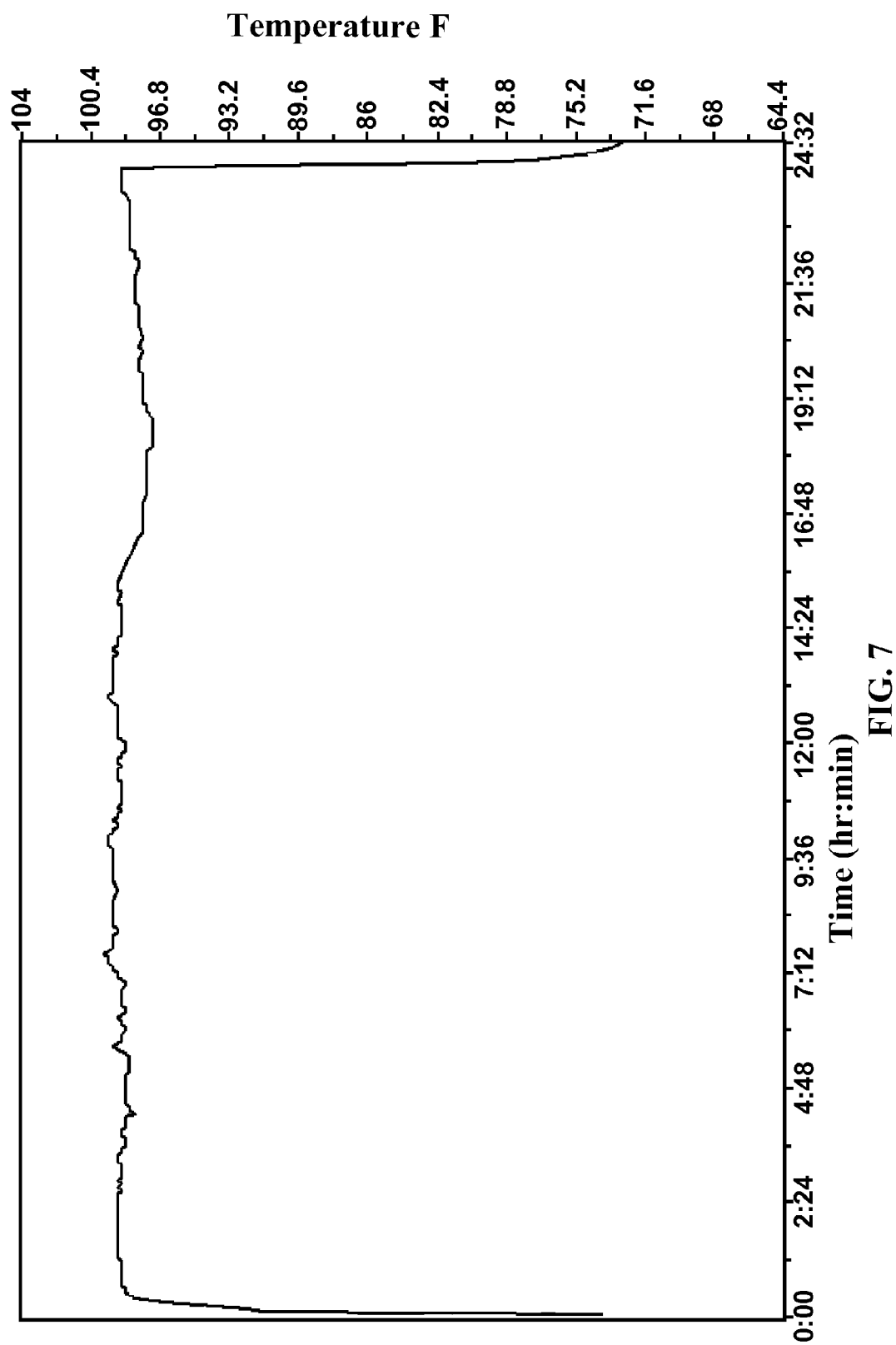
FIG. 7 is a graph of temperature versus time taken by the capsule passing through the gastrointestinal tract.

Computer 19 determines BET using the temperature data. Temperature readings from capsule 20 are plotted against time, as shown in FIG. 7. Computer 19 is programmed to identify the last hour of data received from capsule 20 by receiver 17. The last recorded transmission is labeled as analysis end time, and the time one hour prior to analysis end time is labeled as analysis start time. The program then searches the conditioned temperature measurements between the analysis start time and the analysis end time for a substantial and sustained temperature drop, as shown in FIG. 7. If a substantial temperature drop is identified by this analysis, the beginning of that temperature drop is marked as BET. The beginning of the drop in temperature is identified by determining the average temperature for all the temperature data and then searching backwards through the temperature date for the first temperature sample that is at least 1° C. less than the average. A substantial temperature drip is positively identified if such a drop in temperature of 1° C. or greater from the average is identified in the subject temperature measurements. While in this embodiment, analysis end time is defined as the transmission end time, it is contemplated that analysis end time may be based on other parameters, such as an event that is recorded by the subject, elapsed time after ingestion, a particular recorded parameter, or a time otherwise identified by the user. Also, a discrete change in the pressure profile may be used to confirm body exit. With the determination of BET, and the earlier determination of passage through the ileocaecal junction, CTT is ascertained. WGTT is determined from the time of ingestion and BET. SLBTT is determined from GET and BET SBTT, CTT, SLBTT and WGTT are then compared by computer 19 to a reference as a function of capsule density and/or size to evaluate the subject for constipation, and in particular to differentiate between healthy and constipated subjects based on certain pre-established parameters or cut-off ranges. Thus, in this embodiment as subject is evaluated for constipation by transit times determined from data recorded by a capsule as it moves through the gastrointestinal tract of the subject with a reference template or model. The reference model is a model of expected SBTT, CTT, SLBTT and WGTT for a healthy subject as a function of the density of the capsule. In this embodiment, the reference is expected transit times for a healthy subject given the capsule's density and/or size.

In this embodiment, reference transit time cutoffs for GET, SBTT, SLBTT, CTT and WGTT are based on the fifth and ninety-fifth percentiles of healthy subjects, although it is contemplated that the tenth and ninetieth percentiles may be used. The ranges set forth in Table 1 below provide the transit time cutoff values for identifying individuals with abnormal transit, either too fast or too slow. A subject with a transit time equal to or greater than the $95^{th}$ percentile value is identified as having a slow transit time for that portion of the gastrointestinal tract. A subject with a transit time less than the $5^{th}$ percentile value is identified as having a fast transit time for that portion of the gastrointestinal tract. These transit time cutoff values are used to guide the treatment of the subject. A subject having a slow CTT is treated for STC. A subject who displays symptoms of constipation, as listed in the ROME III criteria, having a normal CTT is treated for normal transit constipation (NTC). A subject having a slow GET is treated for gastroparesis. A subject having a slow SBTT is treated for an abnormal small bowel transit (no named disease state).

TABLE 1

Transit time cutoff ($5^{th}$ and $95^{th}$ percentile)
Values for GET, SBTT, SLBTT, CTT, & WGTT

|  | GET | SBTT | SLBTT | CTT | WGTT |
|---|---|---|---|---|---|
| $5^{th}$ Percentile | N/A | 2.5 hours | 6.5 hours | 2.5 hours | 8.5 hours |
| $95^{th}$ Percentile† | 5 hours | 6 hours | 65 hours | 59 hours | 73 hours |

†Transit time cutoffs are equal to or greater than the value listed.

A study was conducted to assess the correlation between an ingestible capsules efficacy in this evaluation and an estimate based on ROM, and to assess how well the capsule method could discriminate healthy subjects from subjects having some form of constipation. The capsule method was surprisingly effective.

Eighty-one healthy subjects and 67 constipated subjects were studied simultaneously with the capsule method and ROM. After an overnight fast, subjects ingested a 260 Kcal nutrient bar (SmartBar, SmartPill Corporation, Buffalo, N.Y.) that comprised 17% protein, 66% carbohydrates, 2% fat and 3% fiber along with 50 ml of water, which served as a standardized meal for assessment of GET. Next, subjects swallowed a single ROM capsule containing 24 radio opaque markers (SITZMARKS®, Konsyl Pharmaceuticals Limited, Fort Worth, Tex.) followed by capsule 20. Prior to ingestion, capsule 20 was activated and calibrated. After ingestion, the radio frequency signals emitted by capsule 20 were received and stored by receiver 17 worn continuously for the next five days or until capsule 20 had been passed.

After capsule ingestion, subjects were observed for 6 hours to prevent inadvertent ingestion of another meal that could compromise assessment of GET. Thereafter they received a nutrient drink (ENSURE®, Abbott Laboratories, Illinois) and were discharged. All subjects maintained a diary for the next five days in which they recorded bowel movements, stool consistency (Bristol Stool Scale), and time of food intake and symptoms (pain, nausea). Subjects were asked to eat their usual diet and refrain from unaccustomed diet.

A plain x-ray of the abdomen was performed 48 hours after capsule ingestion, and if capsule 20 had been passed, receiver 17 was retrieved, but the subjects remained in the study, continuing their diary and returning at 120 hours (day 5) for an x-ray to check the number of ROM. If the x-ray revealed that the subject had not passed capsule 20, laxatives could be given to facilitate capsule expulsion.

The analysis consisted of measurements of regional and WGTT with capsule system 15 and review of abdominal x-rays performed to assess the number of retained ROM. Pressure, temperature and pH data were recorded and downloaded into computer 19 for analysis to determine CTT and WGTT.

The primary objective was an assessment of the relationship between CTT and WGTT as determined by capsule 20 with the number of retained ROM on day 2 and day 5. This was addressed through estimation and hypothesis testing and Spearman's correlation. The null hypothesis stated that the two devices (ROM and capsule 20) are equivalent as defined by a true correlation of 0.7 or higher and therefore rejection of the null hypothesis would indicate significant disagreement between the devices.

Capsule system 15 determined data for CTT, WGTT and GET were expressed using estimates of quartiles. The upper limit of recorded GET was taken as 6 hours, because all subjects received a second meal at 6 hours. For WGTT the upper limit was 120 hours representing the time of study completion. To accommodate this partial information (some subjects had true WGTT>120 hours), quartile estimates were based on inversion of Kaplan-Meier curve. The differences between constipated subjects and controls for SBTT were assessed using the Wilcoxon rank sum test or the rank based procedure proposed by Gehan, whichever was appropriate. Intra group analyses were conducted to examine the effects of gender, and compared between groups.

The diagnostic utility of capsule system 15 for identifying subjects with constipation symptoms was examined through construction of a receiver operating characteristic curve (ROC). The area under the curve (AUC) was taken as an overall measure of diagnostic accuracy. Similarly, the utility of the ROM test was examined through construction of a ROC curve for the number of ROM remaining on day 5. Statistical differences in diagnostic utility were examined through computation of the 95% bootstrap confidence interval for the difference between the areas under the ROC curves for both tests.

Transit time cutoffs based on the 95th percentile of the healthy control population were used to determine the sensitivity and specificity for capsule 20 determined CTT and WGTT. Day 5 ROM sensitivity and specificity was based on a cutoff of >5 markers retained. A subanalysis of the ROC and sensitivity/specificity of capsule 20 in patients with abnormal transit (>5 ROM on day 5) was also performed. The Chi-square test was used to examine the association between the location of the majority of ROM on day 2 and day 5 x-ray with the location of capsule 20. Interobserver agreement for ROM count was examined through calculation of intra-class correlation and kappa statistic (>5 versus ≤5 retained). All analyses were performed using SAS (version 9.1.3, SAS Institute Inc., Cary, N.C.), and a difference of 0.05 was considered significant.

One hundred and sixty-five subjects were enrolled of whom 78 subjects had constipation [69 females (mean age 45 years, age range 21-79) and 9 males (mean age 53 years, age range 27-78)] and 87 were healthy volunteers [40 females (mean age 39 years, age range 18-66) and 47 males (mean age 36 years, age range 20-72)]. Data from 17 subjects could not be used or was not available. Capsule 20 derived data from 148 subjects, 67 constipated (male/female=8/59) and 81 healthy (male/female=42/39) were available for determining transit times. Two subjects failed to obtain x-rays on day 2/day 5 and ten other subjects had x-rays on day 4 rather than day 5. Thus, ROM data was available in 153 subjects. [86 healthy (male/female=47/39) and 67 constipated (male/female=8/59)].

FIG. 8A shows examples of normal transit in a healthy subject, and delayed CTT with capsule system 15 in a constipated subject is shown in FIG. 8B. The median values for CTT, WGTT, GET and SBTT are shown in Table 2 below.

CTT than controls ($p<0.0001$), irrespective of gender differences between groups. Furthermore, constipated men ($p=0.0264$) and women ($p=0.0023$) also had slower CTT than control men and women. Also, in healthy controls, women had slower CTT than men ($p=0.0080$).

WGTT was slower ($p<0.0001$) in constipated subjects than controls, as shown in FIG. 10. Also, constipated men and women had slower WGTT when compared to gender-based controls (males: $p=0.0115$; females: $p=0.0004$). WGTT was significantly slower in healthy women when compared to healthy men ($p<0.0001$), but there was no gender difference among constipated subjects ($p=0.73$).

Constipated subjects had significantly slower ($p=0.0123$) GET but not SBTT ($p=0.0908$) when compared to healthy controls, as shown in FIG. 10. Also, healthy women had slower GET than healthy men ($p=0.0064$).

Twenty two (37%) constipated subjects retained >5 markers on day 5 x-ray indicating slower CTT. Thus, more ($p<0.0001$) constipated subjects had slower CTT than controls. The median number of ROM that was retained on day 2 x-ray in constipated subjects was 22 and in healthy subjects was 6 ($p<0.0001$), as indicated in Table 3 below. The overall correlation of the number of ROM that was seen on day 2 with

TABLE 2

Median ($25^{th}$-$75^{th}$ percentiles) Values for CTT, WGTT, GET and SBTT As Determined by Capsule System 15 in Constipated Subjects and Healthy Controls (With Effects of Gender).

| | Overall | | | Females only | | | Males only | | |
|---|---|---|---|---|---|---|---|---|---|
| | Constipated (n = 67) | Healthy (n = 81) | p-value | Constipated (n = 59) | Healthy (n = 39) | p-value | Constipated† (n = 8) | Healthy (n = 42) | p-value |
| CTT (Hrs) | 46.7 (24.0-91.9) | 21.7 (15.5-37.3) | <0.0001 | 46.7 (24.0-91.9) | 24.7 (17.3-43.2) | 0.0013 | 50.9 (25.2-) | 18.7 (13.3-26.8) | 0.0264 |
| WGTT (Hrs) | 59.3 (39.7-97.9) | 29.7 (22.4-45.7) | <0.0001 | 58.0 (39.7-97.9) | 33.9 (25.7-51.0) | 0.0004 | 72.2 (36.3-) | 25.6 (20.8-33.9) | 0.0115 |
| GET (Hrs) | 3.5 (3.0-4.2) | 3.0 (2.5-3.9) | 0.0123 | 3.4 (3.0-4.1) | 3.5 (2.7-4.2) | 0.8414 | 4.2 (3.6-) | 2.7 (2.4-3.7) | 0.0054 |
| SBTT (Hrs) | 4.2 (3.5-5.1) | 3.8 (3.2-4.7) | 0.0908 | 4.2 (3.5-5.2) | 3.8 (2.9-4.9) | 0.2530 | 4.4 (3.4-4.8) | 3.8 (3.3-4.5) | 0.4667 |

†Seventy-fifth percentile not observed for CTT, WGTT, and GET due to capping of data.

Figure 9:
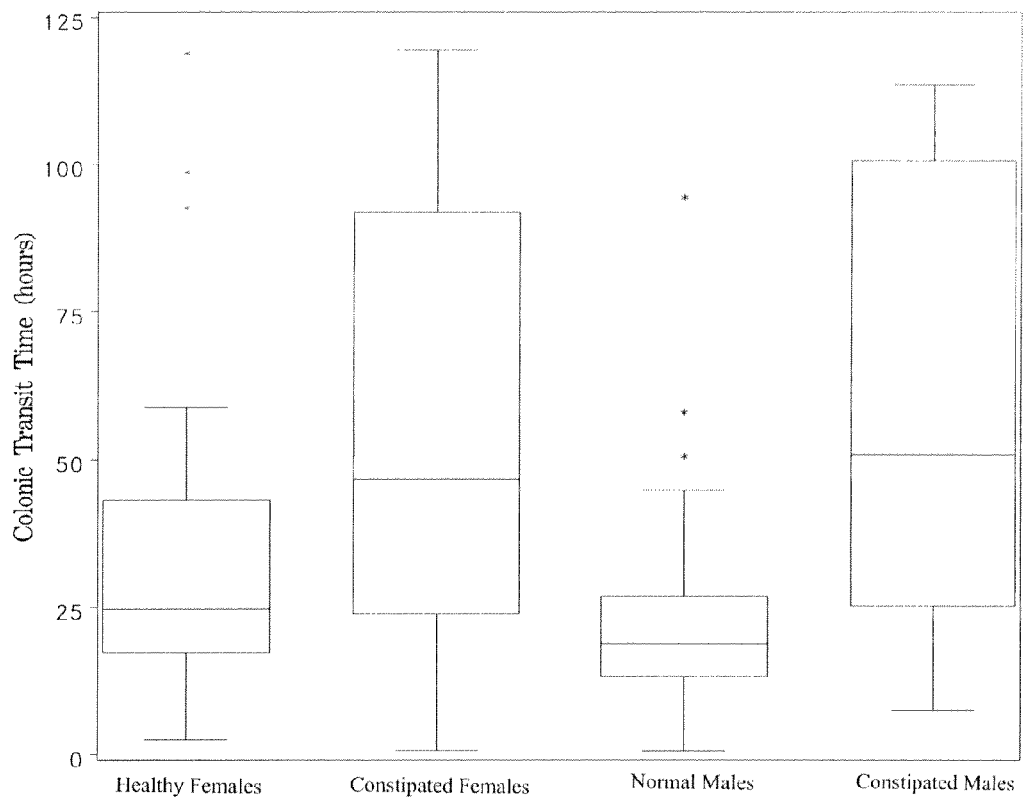
FIG. 9 is box-and-whisker plot of capsule derived CTT in healthy and constipated subjects, and effects of gender. CTT was significantly slower in constipated women and men compared with controls.

FIG. 9 shows the gender-based distribution of CIT. Although there is overlap, constipated subjects had slower that of day 5 was 0.62, and for healthy controls it was 0.44 and for constipated subjects it was 0.58.

TABLE 3

Median Values ($25^{th}$ to $75^{th}$) for the Number of ROMS That Were Retained on Plain Abdomen X-Rays Taken on Day 2 and Day 5 in Constipated Subjects and Healthy Controls (With Effects of Gender).

| | Overall | | | Females only | | | Males only | | |
|---|---|---|---|---|---|---|---|---|---|
| | Constipated | Healthy | p-value | Constipated | Healthy | p-value | Constipated | Healthy | p-value |
| No. of ROM on Day 2 | 22 | 6 | | 22 | 12 | | 15 | 1 | |
| | (9-24) | (1-16) | <0.0001 | (10-24) | (4-21) | 0.0004 | (9-17) | (0-9) | 0.0019 |
| No. of ROM on Day 5 | 1 | 0 | | 1 | 0 | | 1 | 0 | |
| | (0-17) | (0-0) | <0.0001 | (0-17) | (0-1) | 0.0001 | (0-13.5) | (0-0) | 0.0004 |

The Spearman's correlation coefficient between CTT as assessed by capsule system 15 and day 2 x-ray ROM results for the overall sample was r=0.78. When estimated separately, it was found to be 0.74 in constipated subjects and 0.70 in controls. The correlation between CTT and ROM on day 5 for the entire group was 1-0.59 (95% Cl: 0.46, 0.69). The correlation in constipated subjects was r=0.69 and in controls r=0.40. Comparable results were found for the correlation of ROM with WGTT, as indicated in Table 4 below. The lower correlations on day 5 were because many subjects had no ROM on day 5 x-ray.

TABLE 4

Correlation of CTT and WGTT as Measured by Capsule 20 With the Number of Retained ROM.

| SmartPill Parameter | Overall Group Day 2 ROM (CI) | Day 2 ROM Healthy | Day 2 ROM Constipated | Overall Group Day 5 ROM (CI) | Day 5 ROM Healthy | Day 5 ROM Constipated |
|---|---|---|---|---|---|---|
| CTT | 0.78 (0.70-0.84) | 0.70 | 0.74 | 0.59 (0.46-0.69) | 0.40 | 0.69 |
| WGTT | 0.77 (0.68-0.84) | 0.74 | 0.67 | 0.58 (0.45-0.69) | 0.39 | 0.66 |

The location of capsule 20 as revealed by the day 2 or day 5 x-rays was strongly associated (p<0.001) with the region of the colon in which a majority of ROM was seen. For example, the capsule 20 was seen in the left colon in 47 subjects, and in 39 (83%) of these subjects the majority of ROM was seen in left colon.

The diagnostic utility for predicting constipation symptoms is approximately the same for ROM (AUC=0.71) and the capsule system 15 method (AUC=0.73). The area under the ROC curve (AUC) and the gender related sensitivity and specificity values for capsule system 15 derived CTT and WGTT, and day 5 ROM are reported in Table 5 below along with their corresponding cutoffs. A sub-analysis of the ROC, sensitivity and specificity of capsule system 15 for WGTT and CTT in subjects with an abnormal ROM transit revealed an AUC of 0.88 for both measures.

TABLE 5

Area Under the Curve (AUC) of the Receiver Operating Characteristics Curve, Sensitivity and Specificity for Capsule 20 Derived CTT and WGTT, and Day 5 ROMs.

| Parameter | AUC (95% CI) | | Cut Off | Sensitivity | Specificity |
|---|---|---|---|---|---|
| CTT | 0.73 (0.65, 0.82) | All subjects | 59 hr | 0.46 | 0.95 |
| | | Male | 44 hr | 0.50 | 0.90 |
| | | Female | 59 hr | 0.46 | 0.92 |
| WGTT | 0.76 (0.68, 0.84) | All subjects | 73 hr | 0.42 | 0.95 |
| | | Male | 52 hr | 0.63 | 0.90 |
| | | Female | 73 hr | 0.41 | 0.92 |
| Day 5 radioopaque markers | 0.71 (0.63-0.78) | All Subjects | >5 markers | 0.37 | .95 |

The cutoff value for normal versus delayed CTT with the capsule system 15 method in men was 44 hours and in women was 59 hours. As shown in Table 5, the sensitivity and specificity of CTT as measured by capsule system 15 was 0.50 and 0.90 for men and 0.46 and 0.92 for women respectively. Using a cutoff of 5 ROM retained on day 5 as abnormal, the sensitivity and specificity of day 5 ROM was 0.37 and 0.95 respectively.

Twenty three constipated subjects were delayed according to ROM criteria, and 19 of these subjects (83%) also had delayed CTT as measured by capsule system 15. Thirty one constipated subjects were delayed according to CTT criteria (>59 hours) from capsule system 15 and 21 (68%) of these subjects had delayed transit by day 5 ROM criteria.

ROM technique is used commonly for measuring colonic transit, and hence often serves as the gold standard. Surprisingly, capsule system 15 proved to be more sensitive than ROM in detecting slow transit in a subject, and there was good correlation between ROM technique and the capsule system 15 for CTT and WGTT. The data revealed that capsule system 15 had high specificity and reasonable sensitivity for identifying an abnormal transit time in patients with constipation. These values were comparable with the ROM specificity and sensitivity, respectively. Thus, the study overall showed that capsule system 15 can discriminate between subjects with normal and slow colonic transit. The ability to provide a continuous and more direct measure of CTT offers the potential for characterizing the severity of slow transit constipation. In addition, almost 15% of subjects with a diagnosis of chronic constipation had delayed GET.

The present invention contemplates that many changes and modifications may be made. Therefore, while the presently-preferred form of the improved method has been shown and described, and a number of alternatives discussed, persons skilled in this art will readily appreciate that various additional changes and modifications may be made without departing from the spirit of the invention, as defined and differentiated by the following claims.

What is claimed is:

1. A method of evaluating constipation in a subject having one or more symptoms of constipation, said subject having swallowed an ingestible capsule comprising a pH sensor and a temperature sensor, the method comprising the steps of:
    recording pH and temperature measurements from said pH and temperature sensors, respectively, as a function of time as said capsule moves through at least a portion of the gastrointestinal tract of said subject;
    transmitting said pH and temperature measurements to a processor outside of said gastrointestinal tract of said subject, wherein said processor is configured to;
        determine said capsule's location at a first position and at a second position in said gastrointestinal tract as a function of said measurements;
        determine transit time between said first position and said second position to ascertain colonic transit time (CTT) and whole-gut transit time (WGTT);
        provide a reference transit time; and
        compare said CTT and said WGTT to said reference transit time to evaluate said subject for constipation, wherein said constipation is verified when said CTT and WGTT are slower compared to said reference transit time.

2. The method set forth in claim 1, wherein the processor is further configured to determine one or more of gastric emptying time (GET), small bowel transit time (SBTT), and small and large bowel transit time (SLBTT).

3. The method set forth in claim 1, wherein said reference transit time is a function of corresponding transit time of a capsule for a healthy control sample population.

4. The method set forth in claim 1, wherein said subject is identified as having normal transit constipation when said CTT is not slower than said reference transit time and said subject possesses a plurality of said symptoms of functional constipation selected from the group consisting of: straining during at least 25% of defecations; lumpy or hard stools in at least 25% of defecations; sensation of incomplete evacuation for at least 25% of defecations; sensation of anorectal obstruction/blockage for at least 25% of defecations; manual maneuvers to facilitate at least 25% of defecations; fewer than three defecations per week; loose stools which are rarely present without the use of laxatives; and insufficient criteria for irritable bowel syndrome.

5. A method of evaluating constipation in:
a subject having one or more symptoms of constipation,
said subject having swallowed an ingestible capsule comprising a pH sensor, a temperature sensor, and a pressure sensor, the method comprising the steps of:
recording pH, pressure and temperature measurements from said pH, pressure and temperature sensors, respectively, as a function of time as said capsule moves through at least a portion of the gastrointestinal tract of said subject;
transmitting said measurements to a processor outside of said gastrointestinal tract of said subject, wherein said processor is configured to;
determine said capsule's location at a first position and at a second position in said gastrointestinal tract as a function of said measurements;
determine transit time between said first position and said second position to ascertain colonic transit time (CTT) and whole-gut transit time (WGTT);
provide a reference transit time; and
compare said CTT and WGTT to said reference transit time to evaluate said subject for constipation, wherein said constipation is verified when said CTT and said WGTT are slower compared to said reference transit time.

6. The method set forth in claim 5, wherein the processor is further configured to determine one or more of gastric emptying time (GET), small bowel transit time (SBTT), and small and large bowel transit time (SLBTT).

7. The method set forth in claim 5, wherein said reference transit time is a function of corresponding transit time for a healthy control sample population.

8. The method set forth in claim 5, wherein said subject is identified as having normal transit constipation when said CTT is not slower than said reference transit time and said subject possesses a plurality of said symptoms of functional constipation selected from the group consisting of: straining during at least 25% of defecations; lumpy or hard stools in at least 25% of defecations; sensation of incomplete evacuation for at least 25% of defecations; sensation of anorectal obstruction/blockage for at least 25% of defecations; manual maneuvers to facilitate at least 25% of defecations; fewer than three defecations per week; loose stools which are rarely present without the use of laxatives; and insufficient criteria for irritable bowel syndrome.

9. A method for determining the presence and severity of slow colonic transit constipation (SCTC) in a subject having one or more symptoms of constipation, said subject having swalloded an ingestible capsule comprising a temperature sensor and one or both of a pH sensor and a pressure sensor, the method comprising the steps of:
recording measurements from said temperature sensor and one or both of said pH sensor and said pressure sensor as a function of time as said capsule moves through said subject's colon;
transmitting said measurements to a processor external to said subject, wherein said processor is configured to;
determine said capsule's transit time based on a first colonic position and a second colonic position as a function of said measurements;
compare said measurements to a reference transit time;
diagnose the presence of said SCTC based on the comparison, wherein said subject is afflicted with said SCTC if said capsule's transit time is slower than said reference transit time, wherein the slower the capsule's transit time relative to the reference transit time, the more severe the SCTC.

10. The method set forth in claim 9, wherein said reference transit time is a function of corresponding transit time of a capsule for a healthy control sample population.

11. The method set forth in claim 1, wherein said one or more symptoms of functional constipation are selected from the group consisting of: straining during at least 25% of defecations; lumpy or hard stools in at least 25% of defecations; sensation of incomplete evacuation for at least 25% of defecations; sensation of anorectal obstruction/blockage for at least 25% of defecations; manual maneuvers to facilitate at least 25% of defecations; fewer than three defecations per week; loose stools which are rarely present without the use of laxatives; and insufficient criteria for irritable bowel syndrome.

12. The method set forth in claim 5, wherein said one or more symptoms of functional constipation are selected from the group consisting of: straining during at least 25% of defecations; lumpy or hard stools in at least 25% of defecations; sensation of incomplete evacuation for at least 25% of defecations; sensation of anorectal obstruction/blockage for at least 25% of defecations; manual maneuvers to facilitate at least 25% of defecations; fewer than three defecations per week; loose stools which are rarely present without the use of laxatives; and insufficient criteria for irritable bowel syndrome.

13. The method set forth in claim 9, wherein said one or more symptoms of functional constipation are selected from the group consisting of: straining during at least 25% of defecations; lumpy or hard stools in at least 25% of defecations; sensation of incomplete evacuation for at least 25% of defecations; sensation of anorectal obstruction/blockage for at least 25% of defecations; manual maneuvers to facilitate at least 25% of defecations; fewer than three defecations per week; loose stools which are rarely present without the use of laxatives; and insufficient criteria for irritable bowel syndrome.

14. The method set forth in claim 1, wherein said capsule has a density from about 0.026 to about 0.029 grams/cm$^3$.

15. The method set forth in claim 5, wherein said capsule has a density from about 0.026 to about 0.029 grams/cm$^3$.

16. The method set forth in claim 9, wherein said capsule has a density from about 0.026 to about 0.029 grams/cm$^3$.

* * * * *